United States Patent [19]
Buzzolini

[11] 3,931,275
[45] Jan. 6, 1976

[54] BIS(4-(4-HYDROXYBENZYL)PHENYL) CARBONIC ACID ESTER

[75] Inventor: Mario Gustav Buzzolini, Convent Station, N.J.

[73] Assignee: Sandoz Inc., E. Hanover, N.J.

[22] Filed: Dec. 3, 1973

[21] Appl. No.: 420,954

Related U.S. Application Data

[63] Continuation-in-part of Ser. No. 323,299, Jan. 12, 1973, abandoned.

[52] U.S. Cl............... 260/463; 260/613 R; 424/301
[51] Int. Cl.$^2$............... C07C 69/96; C07C 43/20; A61K 31/265
[58] Field of Search............................. 260/463

[56] References Cited
UNITED STATES PATENTS

| | | | |
|---|---|---|---|
| 2,380,130 | 7/1945 | Valentine, Jr. | 260/463 |
| 3,017,424 | 1/1962 | Meyer et al. | 260/463 |
| 3,510,507 | 5/1970 | Bown et al. | 260/463 |
| 3,579,561 | 5/1971 | Meltsner | 260/463 |
| 3,592,837 | 7/1971 | Traber et al. | 260/463 |

OTHER PUBLICATIONS

Hartung et al., "Organic Reactions," Vol. 7, pp. 269, 295–297, 299, (1953).

*Primary Examiner*—Donald G. Daus
*Assistant Examiner*—Diana G. Rivers
*Attorney, Agent, or Firm*—Gerald D. Sharkin; Robert S. Honor; Thomas O. McGovern

[57] ABSTRACT

Bis (4-[4-hyroxybenzyl]phenyl)carbonic acid ester and its pharmaceutically acceptable salts, are useful in the treatment of lipidemia.

3 Claims, No Drawings

BIS(4-(4-HYDROXYBENZYL)PHENYL) CARBONIC ACID ESTER

This application is a continuation-in-part of copending U.S. Pat. application, Ser. No. 323,299, filed Jan. 12, 1973, now abandoned.

This invention relates to the carbonic acid diester of bis-(4-hydroxyphenyl)-methane, methods for preparing the diester, and its use in pharmaceutical compositions.

The compounds of this invention may be represented by the following formula:

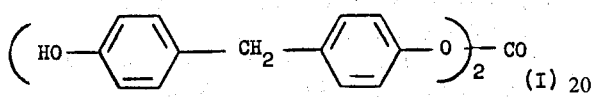

and pharmacologically acceptable salts thereof.

The compound of formula (I) may be prepared in accordance with the following reaction scheme:

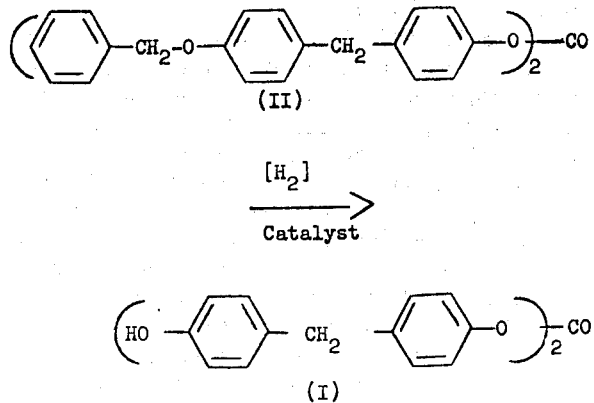

The compound of formula (I) may be prepared by hydrogenating the compound of formula (II) in the presence of a hydrogenation catalyst in an inert solvent. The hydrogenation catalyst is preferably a platinum or palladium catalyst especially 5% platinum or palladium on carbon. The inert solvents preferred are dimethylformamide, dimethylacetamide, esters such as ethyl acetate, the lower alcohols, especially methanol, ethanol, or isopropyl alcohol, and ethers, such as dioxane and tetrahydrofuran or mixtures thereof. The temperature of the reaction and the pressure of the hydrogen are not critical in the hydrogenation. The process can be carried out at a temperature of about 0° to 50°C., preferably 20° to 30°C., especially between 20° and 25°C. The process is carried out preferably at pressures which vary from about 14 psi (about 1 atmosphere) to about 50 psi. Compound (I) is recovered by conventional techniques, e.g., by chromatography or recrystallization.

The compound of formula (I) form pharmacologically acceptable salts with such cations as sodium, potassium, calcium, magnesium and the like and such salts are included within the scope of the present invention. The salts are prepared by conventional techniques, e.g., by dissolving the ester in a suitable solvent, e.g., water or lower alkanol such as methanol, ethanol and the like or in a mixture of water and lower alkanol and treating the ester with an oxide or hydroxide of the desired cation. Conversely the salts are converted back to the esters by treatment with an acid e.g., sulfuric acid, hydrochloric acid, and the like in a similar solvent. The compound of formula (I) contains two centers for salt formation and may therefore form mono or di-salt forms. This invention is intended to embrace both mono and di-salt forms but the di-salt forms are preferred. The disodium salts are especially preferred.

The compound of formula (II) may be prepared in accordance with the following reaction scheme:

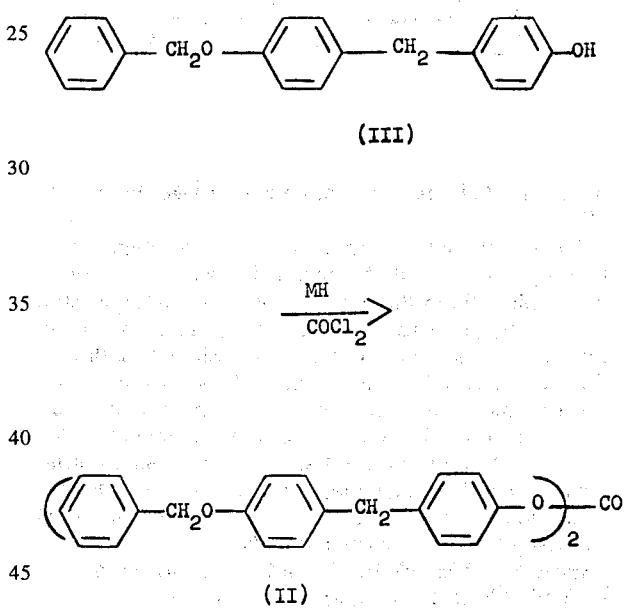

where MH is an alkali metal hydride

The compound of formula (II) is prepared by treating compound (III) with phosgene in an inert solvent in the presence of an alkali metal hydride. The alkali metal hydride used in the reaction can be any alkali such as sodium, lithium or potassium hydride preferably sodium hydride. Although the particular solvent used in not critical, the preferred inert solvents are hydrocarbons, e.g., hexane, benzene, toluene, and the like, dimethylformamide, dimethylacetamide or ethers such as dioxane or tetrahydrofuran. The temperature is not critical but it is preferred that the reaction be carried out between 0° to 50°C especially 20° to 30°C. The time of the reaction is also not critical, but it is normally run for about 1 hour to 24 hours. The product (II) is recovered by conventional techniques, e.g., extraction and evaporation.

The compound of formula (III) may be prepared by the following reaction scheme:

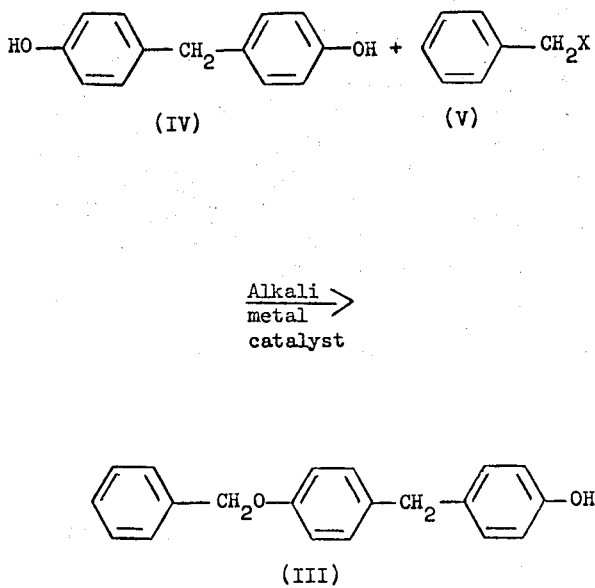

where X is halo having an atomic weight of about 35 to 80.

The compound of formula (III) can be prepared by treating a compound of formula (IV) with a compound of formula (V) in the presence of an alkali metal such as sodium, potassium, and the like; alkali metal hydrides, such as sodium hydride, potassium hydride and the like; or an alkali metal salt such as potassium carbonate, preferably sodium or sodium hydride. Although a solvent is not required, it is preferred that the reaction be run in an inert solvent e.g. dimethylformamide, dimethylacetamide, ethers such as tetrahydrofuran and the like, or acetone when the alkali metal catalyst is potassium carbonate. The temperature is not critical, but it is preferred that the reaction be run at between about 0° to about 150°C, especially between 20° to 100°, in particular, 20° to 30°. The time of the reaction also is not critical, but it is preferred that the reaction should be run for at least 30 minutes. Because the above reaction also yields the dibenzyl ether, the monobenzyl ether (III) must be separated from it. This can be done by standard techniques, for example, crystallization and column chromatography.

The compounds of formula (IV) and (V) are known and may be prepared by techniques which are disclosed in the literature.

The compound of formula (I), and its pharmaceutically acceptable salts, are useful because they possess pharmacological activity in animals. In particular, the compound of formula (I) and its pharmaceutically acceptable salts are useful as hypolipidemic agents in the treatment of lipidemia, in particular, hyperlipoproteinemia, as indicated by the fall in cholesterol and triglyceride levels in male albino Wistar rats weighing 110–130g initially. The rats are maintained on drug-free laboratory chow diet for seven days and then divided into groups of 6 to 10 animals. Each group, with the exception of the control, is then given orally 30 to 250 milligrams per kilogram of body weight per diem of the test compound for six days. At the end of this period, the animals are anesthetized with sodium hexobarbital and bled from the carotid arteries. Serum or plasma samples are collected and 1.0 ml of the serum is added to 9.0 ml redistilled isopropanol. Two autoanalyzer cupsful of a mixture of zeolite-copper hydroxide and Lloydds reagent (Kersler, G., and Lederer, H, 1965, Technicon Symposium, Madiad Inc. New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usages, compound (I) or a pharmacologically acceptable salt thereof may be administered orally or parenterally as such or admixed with conventional pharmaceutical carriers of adjuvants. They may be administered orally in such forms as tablets, dispersible powders, granules, capsules, syrups, elixirs, suspensions and the like or parenterally as injectable solutions, suspensions, dispersions, emulsions, and the like. These pharmaceutical preparations may contain up to about 90% of the active ingredient in combination with the carrier or adjuvant.

The hypolipidemic effective dosage of active ingredient employed for the treatment of lipidemia, in particular hyperlipoproteinemia may vary depending on the particular compound employed, the mode of administration and the severity of the condition being treated. However, in general, satisfactory results are obtained when compound (I) or a pharmaceutically acceptable salt thereof is administered at a daily dosage of from about 4 milligrams to about 250 milligrams per kilogram of animal body weight, preferably given in divided doses two to four times a day, or in sustained release form. For most large mammals, the total daily dosage is from about 300 to about 3000 milligrams. Dosage forms suitable for internal use comprise from about 75 to about 1500 milligrams of the active compound in intimate admixture with a solid or liquid pharmaceutically acceptable carrier or diluent.

The preferred pharmaceutical compositions from the standpoint of preparation and ease of administration are solid compositions, particularly hard-filled capsules and tablets containing from about 200 to 500 milligrams of the active ingredient.

A representative formulation suitable for oral administration is a capsule prepared by standard encapsulating techniques which contains the following and may be administered 2 to 4 times a day in the treatment of lipidemia:

| Ingredients | Weight (mg) |
| --- | --- |
| bis(4-[4-hydroxybenzyl]phenyl carbonic acid ester | 250 |
| Inert filler (lactose, kaolin, starch) | 250 |

EXAMPLE 1

Bis (4-[4-hydroxybenzyl]phenyl)carbonic acid ester

Step A: α-(p-benzyloxyphenyl)-p-cresol

To a stirred suspension of 3.36 g of sodium hydride (in mineral oil) in 50 ml of dimethylformamide is added dropwise at room temperature a solution of 15 g bis-(p-hydroxyphenyl)-methane in 50 ml dimethylformamide. The resulting solution is stirred at room temperature for one hour. Ten grams of benzyl chloride is added dropwise and the stirring is continued at room temperature overnight. After evaporation of the solvent under reduced pressure, the residue is treated with 100 ml of water and extracted twice with diethyl ether. The combined ether extracts are combined, dried over anhydrous magnesium sulfate, evaporated to dryness, and the resulting oil dissolved in hot ethanol. Bis(p-(benzyloxy)phenyl)methane crystallizes upon cooling and is collected by filtration. The mother liquors are evaporated to dryness and the crystalline mono-addition product is obtained by chromatography on silica gel with chloroform. After separation, the mono-benzyl ether is recrystallized from isopropyl ether, m.p. 95°–96°C.

Step B: Bis (4-[4-benzyloxybenzyl]phenyl)carbonic acid ester

To a stirred suspension of 0.93 grams of sodium hydride in 25 ml. of anhydrous benzene is added dropwise at room temperature a solution of 5.8 grams of α-(p-benzyloxyphenyl)-p-cresol in 25 ml. of anhydrous benzene. The resulting solution is stirred at room temperature for one hour and 8.61 grams of a 12% solution of phosgene in benzene is added dropwise at 10°C. After the addition is completed, the reaction mixture is stirred at room temperature overnight. Following evaporation of the excess phosgene and the solvent under reduced pressure, the residue is treated with water and extracted twice with diethyl ether. The combined ether extracts are combined, dried over anhydrous magnesium sulfate and evaporated to dryness yielding the title product as a white solid.

Step C: Bis (4-[4-hydroxybenzyl]phenyl)carbonic acid ester

A solution of 3.1 grams of the above bis (4-[4-benzyloxybenzyl] phenyl)carbonic acid ester in 50 mg. of dimethyl formamide is hydrogenated over 3 grams of 5% palladium on charcoal at atmospheric pressure and room temperature. The catalyst is then separated by filtration through celite and the solvent evaporated. The oil obtained is chromatographed through silica gel with chloroform/methanol 95:5 yielding a colorless oil which is recrystallized from ethanol/water to yield the title product, m.p. 156°–158°C.

The bis (4-[4-hydroxybenzyl]phenyl)carbonic acid ester of this example is an effective hypocholesterolemic agent when administered orally at a dosage of 250 milligrams twice a day.

What is claimed is:

1. The compound of the formula

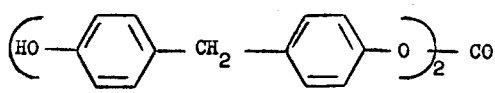

2. The compound of claim 1 in the form of its pharmacologically acceptable salts.

3. The compound which is bis (4-[4-benzyloxybenzyl]-phenyl) carbonic acid ester.

* * * * *